United States Patent [19]

Hayashi et al.

[11] Patent Number: 5,004,609

[45] Date of Patent: Apr. 2, 1991

[54] FIBRINOPHILIC UROKINASE COMPLEX

[75] Inventors: Shigeru Hayashi; Kaneo Yamada, both of Tokyo, Japan

[73] Assignee: Shiseido Company Ltd., Tokyo, Japan

[21] Appl. No.: 403,895

[22] Filed: Sep. 5, 1989

Related U.S. Application Data

[63] Continuation of Ser. No. 199,250, May 26, 1988, abandoned, which is a continuation of Ser. No. 919,149, filed as PCT JP85/00673 on Dec. 6, 1985, published as WO86/03973 on Jul. 17, 1986, Pat. No. 4,851,345.

[30] Foreign Application Priority Data

Jan. 14, 1985 [JP] Japan .................................. 60-4530

[51] Int. Cl.$^5$ ...................... A61K 37/547; C12N 9/00
[52] U.S. Cl. ................................. 424/94.3; 424/94.63; 424/543; 435/215; 435/226; 435/188
[58] Field of Search .................... 424/543, 94.3, 94.63; 435/215, 226, 188

[56] References Cited

U.S. PATENT DOCUMENTS 4,258,030 3/1981 Sasaki et al. ...................... 424/94.63

FOREIGN PATENT DOCUMENTS 158946 5/1980 Japan .

OTHER PUBLICATIONS

Stump et al, J. Biol. Chem., vol. 216 (3), 1-25-86, pp. 1267-1273.
Kruithof et al, Blood, vol. 64(4), Oct. 1984, pp. 907-913.
Astedt et al, cited in Biol. Abstracts, 80(3), 19105, 1985.
Cieplak et al, Thromb. Haemostasis 53(1), 1958, pp. 36-41.
Clemmenson et al, Protides Biol. Fluids, Proc. Colloq. 1975 (pub. 1976), 23, pp. 39-42.
Sumi et al, cited in Chem. Abstracts 96(3):165202h, 1982.

*Primary Examiner*—Jacqueline Stone
*Attorney, Agent, or Firm*—Cushman, Darby & Cushman

[57] ABSTRACT

This invention discloses a fibrinophilic urokinase complex which is a complex of urokinase with a urokinase inhibitor or tissue activator inhibitor and has a molecular weight of 97,500±3,000 and a method for the production of this fibrinophilic urokinase complex from urine. The urokinase complex can be used, as a thombolytic agent exhibiting an outstanding ability to dissolve thrombus.

8 Claims, 2 Drawing Sheets

FIBRINOPHILIC UROKINASE COMPLEX

This is a continuation of application Ser. No. 199,250, filed May 26, 1988, now abandoned, which is a continuation of application Ser. No. 919,149, filed as PCT JP85/00673 on Dec. 6, 1985, published as WO86/03973 on Jul. 17, 1986, now U.S. Pat. No. 4,851,345.

TECHNICAL FIELD

This invention relates to a fibrinophilic urokinase complex and a method for the production of the complex. More particularly, this invention relates to a fibrinophilic urokinase complex having high affinity for fibrin and exhibiting an excellent thrombolysis and a method for the production of this fibrinophilic urokinase complex from the human urine.

BACKGROUND ART

The urokinase (UK) is one of the plasminogen-activating factors discovered in the urine and is formed biosynthetically in the kidney and discharged into the urine. It acts specifically on plasminogen, displaying an activity of cleavaging the arginyl-valyl (Arg-Val) bond in the molecule of plasminogen and consequently converting the plasminogen into plasmin. Since the plasmin has an ability to dissolve fibrin clots formed in the blood, i.e. the ability to cause the phenomenon of fibrinolysis, the urokinase is widely used as a thromboltic agent for the treatment of such thromboses as cerebral thrombosis, cardiac infarction, and pulmonary embolism and is used in combination with a anti-tumor agent [such as, for example, Mitommycin C (proprietary medicine)]. Since the urokinase is not efficiently absorbed through the gastrointestinal tract, it is administered through intravenous injection or infusion.

When the urokinase is administered in vivo, it activates plasminogen to form plasmin and, in the meantime, it is quickly affected by various inhibitors present in the blood. Particularly, antiplasmins such as an $\alpha_2$-plasmin inhibitor which are produced in large amounts in the blood against the formation of plasmin indirectly inactivate the urokinase by forming complexes with the plasmin which has been activated by the urokinase. Further, the half life in the blood of the urokinase itself is about 15 minutes, a relatively short duration. The fibrinolytic activity exhibited by the urokinase in vivo does not last sufficiently. Since the urokinase has poor affinity for fibrin, it activates plasminogen and forms plasmin near the fibrin clots only with great difficulties and, therefore, fails to provide effective fibrinolysis in the blood. For the urokinase to manifest its thrombolytic activity as desired, it is necessary that the concentration of the urokinase in the blood should exceed a certain threshold value. This necessity has encouraged development of the recent high dose-administration therapy. Unfortunately, however, this therapy has not proved to give an ample clinical effect.

Recently, adoption of tissue activator (T-PA) and single-chain urokinase (SC-UK) as thrombolytic agents of high affinity for fibrin has come to be contemplated. They are expected to provide a higher clinical effect than the urokinase described above. They, however, has the disadvantage that their components of high clinical effect have relatively low levels of specific activity and manifest poor stability. Further, they are produced in low yields. Particularly, the tissue activator has a serious problem that its production is very expensive because it is produced from the tissue of human body as a raw material.

An object of this invention, therefore, is to provide urokinase complex which enjoys high in vivo stability and high affinity for fibrin and a method for the production of the urokinase complex.

Another object of this invention is to provide a fibrinophilic urokinase complex which, as an intravenously or orally administrable thrombolytic agent, proves highly effective clinically and stable and a method for the production of this fibrinophilic urokinase complex from the human urine in a high yield.

DISCLOSURE OF THE INVENTION

The objects described above are accomplished by a fibrinophilic urokinase complex (Fib-UK), which comprises a complex of urokinase with a urokinase inhibitor or tissue activator inhibitor and is characterized by possessing a molecular weight of $97,500 \pm 3,000$.

In the present invention, the urokinase inhibitor or tissue activator inhibitor which forms the complex with urokinase particularly desired to be a placental urokinase inhibitor or a fast acting tissue activator inhibitor.

The objects are also accomplished by a method for the production of a fibrinophilic urokinase complex, characterized by the steps of subjecting human urine to fibrin affinity chromatography and lysine affinity chromatography thereby acquiring a fraction adsorbed by said fibrin affinity chromatography and not adsorbed by the lysine affinity chromatography and isolating from the fraction a substance having a molecular weight of $97,500 \pm 3,000$ and comprising a complex of urokinase with an urokinae inhibitor or tissue activator inhibitor by physical separation method.

This invention discloses a method for the production of a fibrinophilic urokinase complex by the steps of subjecting human urine to fibrin affinity chromatography, immediately subjecting the resultant adsorbed fraction to lysine affinity chromatography, and acquiring an unadsorbed fraction from the latter chromatography. This invention also discloses a method for the production of a fibrinophilic urokinase complex by the steps of subjecting human urine to lysine affinity chromatography, immediately subjecting the resultant unadsorbed fraction to fibrin affinity chromatography, and acquiring the resultant adsorbed fraction. The human urine to be used for this invention is desired to have been deprived of sediment through filtration. The fibrin affinity chromatography in this invention is desired to be performed by the use of a fibrin-celite column or fibrin-agarose column. Further in this invention, the lysine affinity chromatography is desired to be carried out by the use of a lysine-agarose column. In this invention, the fraction which is obtained by the affinity chromatography is desired to be concentrated before it is subjected to physical separation. In this invention, the isolation by physical separation method is desired to be carried out by filtration with a gel or by electrophoresis.

The term "urokinase inhibitor" as used in the present specification is intended to mean such an inhibitor as a placental urokinase inhibitor isolated and purified by Kawano et al. (The Journal of Biochemistry, Vol. 67, No. 3, 1970, pp. 333–342) which possesses high specificity relative to urokinase which is one of the plasminogenactivating factors. The term does not embrace such an inhibitor as $\alpha_2$-plasmin inhibitor, one of the antiplasmins, or an allosteric effector which mainly exhibits high specificity relative to other substances while functioning as an inhibitor relative to urokinase.

The term "tissue activator inhibitor" as used herein is intended to mean an inhibitor which exhibits high specificity relative to a tissue activator, one of the plasminogen-activating factors, which is liberated from the tissue of the endometrial membrane or the uterus. This term does not embrace such an inhibitor as an allosteric effector which mainly exhibits high specificity relative to other substances while functioning as an inhibitor relative to the tissue activator.

The term "urokinase complex" or "urokinase-urokinase inhibitor complex" as used in the present specification is intended to represent the condition in which urokinase bound integrally with an urokinase inhibitor or with a tissue activator inhibitor.

The term "affinity adsorption" or "adsorption" as used in the present specification is intended to mean the condition in which one of two substances mutually exhibiting affinity of biochemical specificity is adsorbed by virtue of the biochemical affinity to an adsorbent formed of the other of the two substances. The term "adsorption", therefore, is to be interpreted in the sense just described unless the term "adsorption" is modified in such a manner as physical adsorption or chemical adsorption.

BEST MODE FOR CARRYING OUT THE INVENTION

Figure 1:
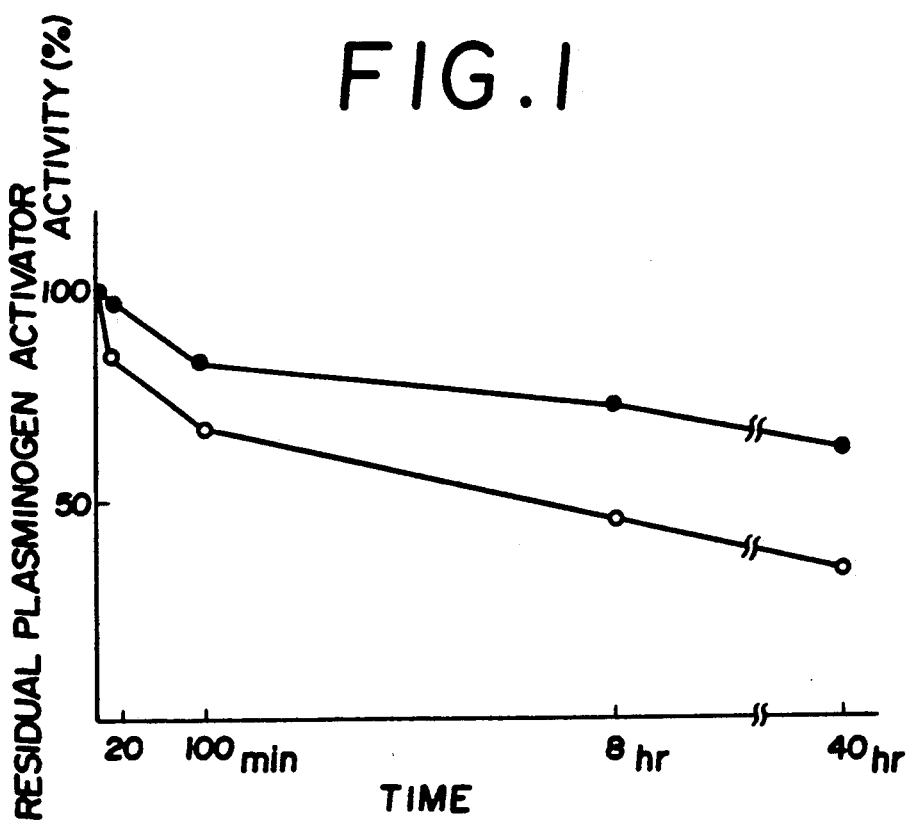
FIG. 1 is a graph showing time-course changes of residual plasminogen activator activity in human blood plasma of a fibrinophilic urokinase complex of this invention and urokinase. In the graph, the line connecting filled circles ● represents the data obtained of the fibrinophilic urokinase complex according to the present invention and the line connecting empty circles (o) the data of urokinase.

Now, the present invention will be described more specifically below with reference to preferred embodiments thereof.

This invention has originated in the discovery that in the fresh human urine, a high molecular substance which functions as an activator relative to plasminogen and exhibits affinity for fibrin is present besides urokinase which known in the general sense of the word. This invention has been perfected in consequence of successful isolation of the substance and identification thereof.

When the high molecular substance of this invention isolated from the human urine by the method to be described in detail afterward is subjected to immunoelectrophoresis, it described sedimentation curves of antiserum relative to a high molecular urokinase (molecular weight about 53,000 to 55,000) and a low molecular urokinase (molecular weight about 31,000 to 33,000). This fact evinces that the substance possesses an antigen common with urokinase. It also describes a sedimentation curve of antiserum relative to a urokinase inhibitor or tissue activator inhibitor. This fact clearly indicates that the substance possesses an antigen common with the urokinase inhibitor or tissue activator inhibitor.

When urokinase and a urokinase inhibitor originating in placenta are intimately mixed and the resultant mixture is subjected to SDS (sodium dodecyl sulfate)-slab electrophoresis and then to zymography by the use of a plasminogen-containing fibrin plate, a dissolution window is recognized at the position of 97,500±3,000, identical with the molecular weight of a dissolution window due to the aforementioned high molecular substance.

Owing to these results of observation, the aforementioned high substance has been identified to be a complex of urokinase with a urokinase inhibitor or tissue activator inhibitor.

Thus, the fibrinophilic urokinase complex of the present invention is characterized by being a complex of urokinase with a urokinae inhibitor or tissue activator inhibitor and having a molecular weight of 97,500±3,000.

Similarly to the ordinary urokinase, the fibrinophilic urokinase complex of the present invention functions as a plasminogen activator and cleaves plasminogen at the location of Arg-Val bond thereof and gives rise to an H chain (molecular weight 55,000), an L chain (molecular weight 26,000), and a decomposed fragment (molecular weight 8,000) respectively of plasmin. The specific activity of the fibrinophilic urokinase complex as a plasminogen activator is about ⅓ to ¼ of that of the oridinary urokinase (high molecular urokinase of a molecular weight of 53,000, to 55,000 and a low molecular urokinase of a molecular weight of 31,000 to 33,000).

The affinity exhibited by the fibrinophilic urokinase complex for fibrin is higher than the oridinary urokinase and equal to or higher than the single-chain urokinase (SC-UK) which is recognized to possess affinity for fibrin. Probably because it is a complex of urokinase with a urokinase inhibitor or a tissue activator inhibitor, the fibrinophilic urokinase complex is so stable as to succumb only minimally to the action of such a substance as an $\alpha_2$-plasmin inhibitor or a serine protease inhibitor which inhibits and inactivates the ordinary urokinase.

When the fibrinophilic urokinase complex is administered in vivo, it exhibits a higher capacity for fibrinolysis and retains this capacity for a longer period than the conventional thrombolytic agent and, therefore, can be expected to produce an excellent clinical effect.

When the fibrinophilic urokinase complex of the present invention is left standing under the condition of room temperature or a low temperature of −20° C. for a long time (about one half year), it undergoes hydrolysis and transforms itself into a substance of a molecular weight on the order of 50,000 to 60,000. The fibrinophilic urokinase complex of the present invention, therefore, is required to be preserved as frozen at a temperature not exceeding −20° C., preferably falling in the range of −40° C. to −80° C., or in a dry frozen state. The dry freezing may be carried out under the conventionally known conditions as by freezing the sample at a temperature of −40° to −80° C. and sublimating the ice from the frozen sample under a vacuum not exceeding 0.3 Torr.

For the fibrinophilic urokinase complex of this invention to be used as a thrombolytic agent, the fibrino philic urokinase complex can be adopted solely or as one of effective ingredient in its unmodified form or in the form of a dilute preparation containing the fibrinophilic urokinase complex in a proper concentration. In this case, the fibrinophilic urokinase complex may, for the purpose of stabilization thereof, incorporate therein any of the known pharmaceutically acceptable vehicles such as albumin, gelatin, and mannitol which are used in the commercially available urokinase preparations.

The in vivo administration of this thrombolytic agent is attained by intravenous injection, intravenous drip infusion, or oral invention, for example. The form of the thrombolytic agent is selected to suit the particular manner of administration. For the purpose of the intravenous administration, it may be prepared in the form of an injections or an drip infusions. For the purpose of oral administration, it may be prepared in the form of capsules, tablets, pills, granules, subtilized granules or powder.

The fibrinophilic urokinase complex of the present invention can be produced in vitro by intimately mixing urokinase with a urokinase inhibitor or tissue activator inhibitor, preferably with a placental urokinase inhibitor or fast acting tissue activator inhibitor and isolating from the resultant mixture the produced urokinase complex by gel filtration, electrophoresis, or affinity chromatography, for example. The fibrinophilic urokinase complex, however, is obtained with better quality and higher purity in a higher yield by a relatively simple procedure at low cost when it is isolation from the human urine as a raw material in accordance with the method to be described below.

To be specific, the isolation is effected by a novel method which comprises the steps of subjecting the human urine to fibrin affinity chromatography and lysine affinity chromatography thereby acquiring a fraction which has been adsorbed through affinity by the fibrin affinity chromatography and has not been adsorbed by the lysine affinity chromatography and isolating from this fraction a substance of a molecular weight of 97,500±3,000 by means of physical separation.

In this method, the sequence in which the fibrin affinity chromatography and the lysine affinity chromatography are carried out can be selected freely. To be more specific, the method may proceed through the procedure of subjecting the human urine to fibrin affinity chromatography, immediately subjecting the resultant fraction of adsorption to lysine affinity chromatography, and acquiring the produced unadsorbed fraction or through the procedure of subjecting the human urine to lysine affinity chromatography, immediately subjecting the produced unadsorbed fraction to fibrin affinity chromatography, and acquiring the produced adsorbed fraction. From the standpoint of yield, however, the method through the latter procedure proves more advantageous. Here, as one embodiment, the method of this invention for the production of the fibrinophilic urokinase complex through the former procedure will be specifically described.

As the raw material for the production by this invention, fresh human urine is used. Desirably, the human urine is filtered for removal of the sediment contained therein before the urine is subjected to the affinity chromatography.

Then, the urine is subjected to fibrin affinity chromatography. As the column for this chromatography, there can be used, a fibrin(monomer)-agarose gel column prepared as reported by D. L. Heene and F. R. Matthias in "Thrombosis Research, Vol. 2, pp. 137–154, 1973, Pergamon Press, Inc. or a fibrin- Celite ® (Celite ®; a proprietary product of diatomaceous earth having $SiO_2$ as backbone) column prepared as reported by S. Shaukat Husain et al. in Proc. Natl. Acad. Sci. USA, Vol. 78, No. 7, pp 4265–4269, July 1981, Biochemistry.

When the urine is passed through the fibrin-Sepharose column which has been equilibrated with a NaCl-phosphate buffer, for example, the urokinase contained in the urine is not adsorbed on the column because it shows no affinity for fibrin, while the fibrinophilic urokinase complex is strongly adsorbed thereon by virtue of the specific affinity for fibrin. The fibrinophilic urokinase complex which has been adsorbed on the column is not eluted even with 0.5 M NaCl but is eluted as with 0.2 M arginine or 6 M urea. The adsorbate on the adsorption column, therefore, is eluted by first washing the adsorption column with 0.01 M phosphate buffer containing 1 mM EDTA and 0.5 M NaCl thereby removing unadsorbed substance and physically adsorbed substance from the column and thereafter treating the adsorption column with 0.01 M phosphate buffer containing 1 mM EDTA and 0.2 M arginine and adjusted to pH 7.6. In the adsorbed fraction obtained as described above, there are contained other substances than the fibrinophilic urokinase complex such as, for example, plasmin, plasminogen, tissue activator, and single-chain urokinase which are present from the beginning in the urine and which exhibit specific affinity for fibrin.

Then, the adsorbed fraction of the fibrinophilic urokinase complex is subjected to lysine affinity chromatography. As the column for this chromatography, there can be used a lysine-agarose gel column as reported by D. G. Deutsch and E. T. Mertz in "Science," 170, 1095 (1970). When the fraction is passed through the lysine-agarose gel column which has been equilibrated with a NaCl-phosphate buffer, for example, the plasmin, plasminogen, and tissue activator contained in this fraction are adsorbed by the column because they exhibit affinity for lysine, whereas the fibrinophilic urokinase complex and the single-chain urokinase are not adsorbed because they exhibit no affinity. The urokinase exhibits affinity for the lysine-agarose gel probably because it possesses an esterase activity causing hydrolysis of methyl esters of lysine and arginine. When the lysine affinity chromatography is carried out before the fibrin affinity chromatography, therefore, the urokinase present in the urine is contained in the adsorption fraction of the lysine affinity chromatography. In the lysine affinity chromatography, the unadsorbed fraction or the crude fibrinophilic urokinase complex fraction which has passed through the lysine-agarose gel column is collected to be forwarded to the subsequent step. Also when the urine is subjected to lysine affinity chromatography and the produced unadsorbed fraction is immediately subjected to fibrin affinity chromatography to acquire the adsorbed fraction, this adsorbed fraction similarly comprises a crude fibrinophilic urokinase complex fraction.

The fraction so acquired is desirably concentrated as by treatment with a dehydrator such as polyethylene glycol or by freeze drying.

This crude fibrinophilic urokinase complex fraction is further treated by a technique of physical separation to effect the isolation of the fibrinophilic urokinase complex. Since the fibrinophilic urokinase complex contained in the fraction is a high molecular substance and the single-chain urokinase and other substances not desired to be isolated are compounds of relatively low molecular weights, the technique of physical separation used for this treatment is desired to make use of the difference in physical properties. For example, the technique resorting to gel filtration or that resorting to electrophoresis can be adopted. As the method of electrophoresis, the method of electrophoresis using a separation gel (preparative gel electrophoresis system) or the method which comprises subjecting the sample to SDS-electrophoresis and then recovering the isolated substance by means of a protein recovering device can be used.

Now, the present invention will be described more specifically below with reference to working examples.

EXAMPLE 1

Isolation of fibrinophilic urokinase complex from urine (I)

Under a low-temperature condition (4° C.), 4 liters of fresh urine was collected and suction filtered through a filter paper (Toyo filter paper No. 2). The filtered urine was added to a lysine-Sepharose column (gel capacity 20 ml) equilibrated in advance with 0.01 M phosphate buffer (pH 7.6) and the fraction which had passed through the lysine-sepharose column was collected. Then, this fraction was added to a fibrin-sepharose column (gel capacity 40 ml, equilibrated in advance with 0.01 M phosphate buffer of pH 7.6). The column was thoroughly washed with 0.01 M phosphate buffer (pH 7.6) containing 1 mM of EDTA and 0.5 M NaCl. Then, the proteins adsorbed on this column were eluted with 0.01 M phosphate buffer (pH 7.6) containing 1 mM EDTA and 0.2 M arginine. Finally, the eluted fraction was concentrated with polyethylene glycol and the resultant concentrated fraction (2 ml) was added to Sephadex G-100 (gel capacity 2.0×90 ml, equilibrated in advance with a 0.01 M phosphate buffer, pH 7.6) and subjected to gel filtration with a 0.01 M phosphate buffer, pH 7.6. The fibrinophilic urokinase complex was eluted (at a molecular weight position level of 97,500±3,000) with a main peak described in the first half part and the single-chain urokinase was eluted, though slightly, in the latter half part. The amount of the fibrinophilic urokinase complex so obtained was 0.51 mg.

EXAMPLE 2

Isolation of fibrinophilic urokinase complex from urine (II)

Under a low-temperature condition (4° C.), 4 liters of fresh urine was collected and suction filtered through a filter paper (Toyo filter paper No. 2). The filtered urine was added to a fibrin-Sepharose column (gel capacity 40 ml) equilibrated in advance with a 0.01 M phosphate buffer, pH 7.6. This column was thoroughly washed with 0.01 M phosphate buffer (pH 7.6) containing 1 mM EDTA and 0.5 M NaCl. Then, the proteins adsorbed on this column were eluted with 0.01 M phosphate buffer (pH 7.6) containing 1 mM EDTA and 0.2 M arginine. Subsequently, the eluted fraction was added to a lysine-Sepharose column (gel capacity 20 ml) equilibrated in advance with 0.01 M phosphate buffer, pH 7.6 and the fraction which had passed through the lysine-Sepharose column was collected. Finally, the unadsorbed fraction was concentrated with polyethylene glycol and the resultant concentrated fraction (2 ml) was added to Sephadex, G-100 (gel capacity 2.0×90 ml, equilibrated in advance with 0.01 M phosphate buffer, pH 7.6) and subjected to gel filtration with 0.01 M phosphate buffer, pH 7.6. The fibrinophilic urokinase complex was eluted (at a molecular weight level of 97,500±3,000), with a main peak described in the first half part and the single chain urokinase was eluted, though slightly, in the later half part. The amount of the fibrinohpilic urokinase complex so obtained was 0.32 mg.

EXAMPLE 3

Identification of fibrinophilic urokinase complex

EXAMPLE 3.1

Method of immunoelectrophoresis

On a flat glass plate, a gel for phoresis was prepared by applying 0.05 M Veronal buffer (pH 8.6, $\mu=0.06$) containing 1% agarose until the thickness of agarose gel increased to about 1 mm. On the gel, a spot for addition of a 10 $\mu$l sample is formed and 10 $\mu$l of a sample was added to the spot. A 0.05 M Veronal buffer (pH 8.6, $\mu=0.06$) was prepared for electrophoresis and the glass plate was immersed therein in such a manner that the opposite ends of the agarose gel were wetted with the phoretic buffer through a filter paper. The electrophoresis was carried out at a fixed voltage of 150 V for about 2 hours. On the gel, a groove was formed along the lateral part of the moved sample parallelly to the direction of phoresis. An antiserum was placed in the groove and left standing overnight in an incubator at 37° C. On the following day the sedimentation curves described by the phoresis, sample and the antibody were observed visually or with the aid of an immunoviewer.

From the results of the experiment described above, it was confirmed that fibrinophilic urokinase complexes obtained in Example 1 and Example 2 both shared antigenicity with urokinase and also shared antigenicity with urokinase inhibitor or tissue activator inhibitor.

EXAMPLE 3.2

Zymography

A suspension of the fibrinophilic urokinase complex obtained in Example 1 in a 0.01 M phosphate buffer was mixed equivoluminally with a 0.5 M Tris buffer containing 10% SDS (sodium dodecyl sulfate) and 50% glycerin so as to be combined with SDS. Then, the resultant mixture was subjected to electrophoresis with a current of 8 mA at 4° C. for about 16 hours by the SDS-polyacrylamide gel slab electrophoretic method (10% gel, 14×14×0.2 cm in size) using a 0.025 M Tris-0.19 M glycine buffer (pH 8.3) containing 0.1% SDS. After the phoresis, the opposite ends of the gel parallel to the direction of phoresis were cut off each in a width of about 5 mm. The cut ends were immersed in 2.5% Triton X-100 for one hour and then washed with water for removal of SDS. The gel, with the adhering water removed with a filter paper, was superposed on a plasminogen-containing fibrin plate and incubated at 37° C. for 15 hours. As the result of the incubation, a lysis area was detected at a molecular weight level of 97,500±3,000.

Separately, 6 units of urokinase and 6 units of placental urokinase inhibitor (made by Green Cross Co., Ltd.) were intimately mixed in a 0.01 M phosphate buffer and then incubated at 30° C. for 20 minutes. Then, the resultant reaction solution was combined with SDS by the same method as described above. It was then subjected to the SDS-polyacrylamide gel slab electrophoresis under the same conditions. Consequently, a zymogram was obtained on a plasminogen-containing fibrin plate. As the result, similarly to the fibrinophilic urokinase complex obtained in Example 1, a lysis area was detected at on a molecular weight level of 97,500±3,000.

The plasminogen-containing fibrin plate used in this experiment was prepared as follows.

Plasminogen-containing fibrin plate

Preparation of plasminogen-containing fibrin plate

In 10 ml of a thrombin solution [a 5 mM phosphate buffer (pH 7.2) containing 0.85% NaCl, 10 U/ml] kept warmed at 45° C., 20 ml of agar solution [a 5 mM phosphate buffer (pH 7.2) containing 0.85% NaCl, 25 mg/ml] and 100 μl of a plasminogen solution [a 5 mM phosphate buffer (pH 7.2) containing 0.85% NaCl, 500 CU*/ml)] were intimately mixed. The resultant mixture and 10 ml of a fibrinogen (bovine, type 2**) solution [a 5 mM phosphate buffer (pH 7.2) containing 0.85% NaCl, 0.4%] added thereto were gently stirred until uniformity. The thorough mixture so obtained was poured in a rectangular dish (made by Eiken, 225×75×15 mm in size) and left cooling and solidifying at room temperature. The plasminogen-containing fibrin plate had a fibrin concentration of 0.1% and a plasminogen concentration of 25 CU/ml.
* Casein unit ** Daiichi Kagaku Yakuhin

EXAMPLE 4

Determination of enzymatic constants of fibrinophilic urokinase complex

For determination of the enzymatic constants of the fibrinophilic urokinase complex obtained in Example 1, samples were allowed to react, in concentration of 14.2 μg/ml and 8.0 μg/ml, with a synthetic substrate S-2444 (made by KABI of Sweden) at 37° C. for 15 minutes, with the aid of a 0.05 M Tris buffer (pH 8.8) containing 0.38 M Nacl. For comparison, the enzymatic constants of urokinase were determined under the same conditions. The results are shown in Table 1 below.

TABLE 1

|  | Fibrinophilic urokinase complex | Urokinase |
|---|---|---|
| Michaelis constant*, km (μM) | 74 | 41 |
| Maximum velocity, $V_{max}$ (× $10^{-9}$ mol/min) | 0.57 | 2.00 |
| $K_{cat}(sec^{-1})$ | 3.8 | 11 |
| $K_{cat}/km$ (μm/sec$^{-1}$) | 0.051 | 0.268 |

*The Michaelis constant is calculated in accordance with the Michaelis-Mentene formula.

The fibrinophilic urokinase complex caused no hydrolysis of the synthetic substrate S-2251 and did not dissolve a plasminogen free fibrin plate. It caused dissolution of the plasminogen-containing fibrin plate.

EXAMPLE 5

Confirmation of affinity of synthetic fibrinophilic urokinase complex for fibrin In a 0.01 M phosphate buffer of pH 7.6, 500 units of urokinase and 500 units of placental urokinase inhibitor (made by Green Cross Co., Ltd.) were mixed and incubated at 37° C. for 20 minutes. Then, the resultant reaction solution was mixed equivoluminally with a 0.5 M Tris buffer containing 10% SDS and 50% glycerin so as to be combined with SDS. The resulting solution was subjected to electrophoresis with an electric current of 4 mA at 4° C. for about 15 hours with a separation gel electrophoresis system (preparative electrophoresis system made by Maruzen Oil Biochemical Co., Ltd.) using a 0.025 M Tris-0.19 M glycine buffer (pH 8.3) as a buffer for phoresis. The gel tube was packed with SDS-polyacrylamide gel (10% gel). During the course of the phoresis, the Tris-glycine buffer was injected through the influent inlet of the apparatus at a flow rate of 2 ml/hour and the effluent from the outlet was collected as divided into 1 ml fractions by the use of a fraction collector. Then, a portion of each of the fractions was subjected to the slab electrophoresis similarly to Example 3.2 and placed on the flat plasminogen-containing fibrin plate to determine the position of fractionation of the complex. The effluent fraction of urokinase-urokinase inhibitor was placed in a dialysis tube and dialyzed with water for removal of SDS.

To examine the affinity of the urokinase-urokinase inhibitor complex obtained as described above for fibrin, 10,000 units/ml solutions of the complex and urokinase, each in a volume of 1 ml, were mixed and the mixture was added to a fibrin-Sepharose column (gel capacity 5 ml) equilibrated in advance with a 0.01 M phosphate buffer, pH 7.6. This column was washed with 30 ml of a 0.01 M phosphate buffer (pH 7.6) containing 1 mM EDTA and 0.5 M NaCl. Then, the proteins adsorbed on this column were eluted with a 0.01 M phosphate buffer (pH 7.6) containing 1 mM EDTA and 0.2 M arginine. Parts of the washings and the eluate, parallelly with the aforementioned urokinase-urokinase inhibitor complex and urokinase, were subjected to the slab electrophoresis by following the procedure of Example 3.2 and then placed on the plasminogen-containing fibrin plate to be tested for fibrinolytic activity in the solution.

In the test run using the washings, a lysis area was detected at the same position of phoresis as urokinase. In the test run using the eluate, a lysis area was detected at the same position of phoresis as the urokinase-urokinase inhibitor complex. It was confirmed that the urokinase-urokinase inhibitor complex showed strong affinity for fibrin and adsorbed thereto, whereas urokinase was not adsorbed on fibrin.

EXAMPLE 6

Preservability of fibrinophilic urokinase complex

To examine the preservability of the fibrinophilic urokinase complex obtained in Examples 1 and 2, samples were held under a varying temperature condition (room temperature, −20° C., −40° C., and −80° C.) and tested for change of molecular weight. The molecular weight was determined by subjecting the sample to the salb electrophoresis by following the procedure of Example 3.2, placing the sample on the plasminogen-containing fibrin plate, and testing it for fibrinolytic activity. As the result, the samples preserved a room temperature and at −20° C. were found to have their molecular weight lowered to about 50,000 after about one half year's standing.

EXAMPLE 7

Stability of fibrinophilic urokinase complex in blood (in vitro)

The fibrinophilic urokinase complex obtained in Example 1 and urokinase were each added in vitro to human blood plasma in a concentration of 40 IU/ml and left standing at 37° C. They were sampled along the course of time and the samples were tested for residual plasminogen activator activity by the use of the plasminogen-containing fibrin plate. The results are shown in FIG. 1. As the result, it was confirmed that the residual activity in the case of the fibrinophilic urokinase complex was 83% after 100 minutes' standing and 73% after 8 hours' standing, whereas the residual activity in the case of urokinase was 67% after 100 minutes standing and 46% after 8 hours' standing.

In the test run using urokinase, the residual activity was 34% even after 40 hours' standing. It was confirmed by zymography that the greater part of this residual activity was due to the complex formed between urokinase and the urokinase inhibitor present in the blood plasma.

EXAMPLE 8

Sensitivity to serine protease inhibitor (DFP)

The effects of serine protease inhibitor upon urokinase and the fibrinophilic urokinase complex were examined as follows.

(i) In urine

Fresh urine (within 24 hours of excretion) 200 ml in volume was dialyzed against deionized water for one night, then concentrated with polyethylene glycol to a volume about 1/100 of the original volume, and passed through anti Urokinase-Sepharose (capacity 1 ml). The concentrated urine was then treated with a 0.01 M phosphate buffer (pH 7.6) containing 1 M NaCl to effect removal therefrom of unadsorbed substance and then eluted with a 0.17 M glycine-hydrochloride buffer, pH 2.3. The resultant eluate was immediately neutralized with 0.5 M carbonate buffer, pH 9.5.

By addition of DFP, 25 μl of the sample prepared as described above was diluted to 25 mM. The diluted sample was heated at 37° C. for one hour. The treated sample was subjected to zymography by following the procedure described above.

(ii) In blood plasma

Human blood plasma 500 μl in volume and 9 IU of urokinase added thereto were incubated at 37° C. for 20 minutes. The resultant mixture was diluted by addition of a 0.01 M phosphate buffer (pH 7.6) to a total volume five times the original volume. The diluted mixture was passed through anti Urokinase-Sepharose (capacity 0.1 ml). The adsorbate was deprived of unadsorbed substance by treatment with a 0.01 M phosphate buffer (pH 7.6) containing 0.5 M NaCl and then eluted with a 0.17 M glysine-hydrochloride buffer, pH 2.3. The resultant eluate was immediately neutralized with a 0.5 M carbonate buffer of pH 9.5.

By addition of DFP, 100 μl of the sample so prepared was diluted to 10 mM. The diluted sample was heated at 37° C. for 20 minutes. The treated sample was then subjected to zymography by following the procedure described above.

As the result, it was confirmed that, in either the urine or the blood plasma, the free urokinase (comprising low molecular urokinase of MW 33,000 and high molecular urokinase of MW 55,000) has its activity inhibited by the serine protease inhibitor, while the fibrinophilic urokinase complex had its activity not inhibited at all by the inhibitor. This is probably because the urokinase complex possesses a molecular structure such that the serine active site exposed on the surface of the molecule of urokinase is protected by being bound with the urokinase inhibitor.

EXAMPLE 9

In vivo durability of fibrinophilic urokinase complex in murine blood

Urokinase and the fibrinophilic urokinase complex obtained in Example 1 were independently administered to rats by intravenous injection for comparison of their half life.

Samples of urokinase and the fibrinophilic urokinase complex were administered in a dose of 10,000 units/0.5 ml saline to male rats of Wistar strain through injection into the tail vein. After the administration, blood was collected from the inferior vena cava into a 3.8% citric acid (1/10 volume) containing aprotinin (50 KIE/ml). The citrated blood was centrifuged at 4° C. at 3,000 rpm for 10 minutes to obtain blood plasma. The citrated plasma was tested for urokinase activity by the method using a synthetic substrate S-2444.

Figure 2:
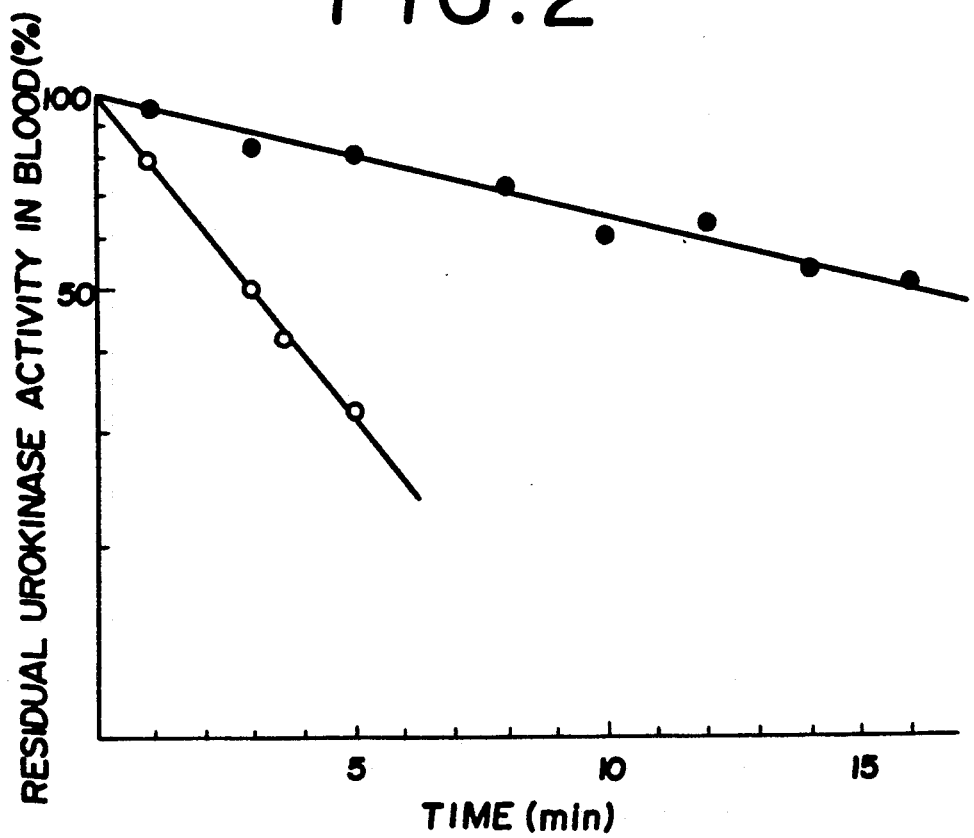
FIG. 2 is a graph showing durations of existence in the blood of rats of the fibrinophilic urokinase complex and urokinase. In the graph, the line connecting filled circles ● represents the data obtained of the fibrinophilic urokinase complex and the line connecting empty circles (o) the data of urokinase.

The results are shown in FIG. 2. It is confirmed that the fibrinophilic urokinase complex of the present invention enjoys high durability in blood, exhibiting a half life of about 16 minutes compared with a half life of about 3 minutes exhibited by urokinase.

The values reported represent averages of the numerical values each obtained in three rats.

EXAMPLE 10

In vivo durability of fibrinophilic urokinase complex in blood of beagles

Urokinase and the fibrinoptilic urokinase complex obtained in Example 1 were independently administered to beagles by intravenous injection for comparison of their half life.

Samples of urokinase and the fibrinophilic urokinase complex were administered in a does of 60,000 units/5 ml saline to beagles weighing about 10 kg each through injection into the vein of the right hind leg. After the administration, blood was collected from the vein in the forearm into aprotinin containing citric acid by following the procedure of Example 9. The citrated plasma was tested for urokinase activity by the method using a synthetic substrate S-2444.

Figure 3:
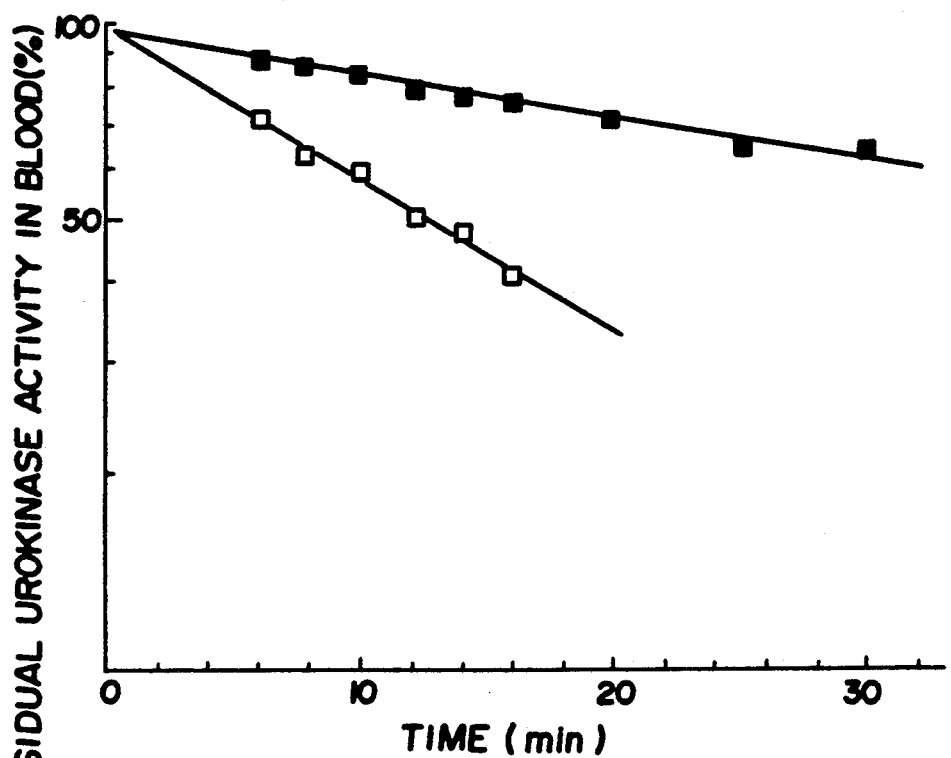
FIG. 3 is a graph showing durations of existence in the blood of beagles of the fibrinophilic urokinase complex and urokinase. In the graph, the line connecting filled squares ■ represents the data obtained of the fibrinophilic urokinase complex and urokinase and the line connecting empty squares (□) the data obtained of urokinase.

The results are shown in FIG. 3. It is confirmed that the fibrinophilic urokinase complex of the present invention enjoys high durability in blood, exhibiting a half life of about 45 minutes compared with a half life of about 13 minutes exhibited by urokinase.

The values reported represent averages of the numerical values each obtained in three beagles.

EXAMPLE 11

Production of injections (I)

Through a membrane filter, a mixture of 24,000 units of the fibrinophilic urokinase complex obtained in Example 1 with 10 mg of purified gelatin and 100 mg of mannitol was sterilely filtered. The filtrate was dispensed into sterilized vials, prefrozen at −60° C. for one hours, and freeze dried at 25° C. under 0.1 Torr for 24 hours, to produce a freeze dried injections.

EXAMPLE 12

Production of injections (II)

A freeze dried injections was produced by following the procedure of Example 12, except that 60,000 units of the fibrinophilic urokinase complex obtained in Example 1 was mixed with 20 mg of human serum albumin and 200 mg of mannitol.

EXAMPLE 13

Production of capsules

The fibrinophilic urokinase complex obtained in Example 1 was freeze dried. Hard capsules of gelatin, No. 2 were filled with a mixture of 30,000 units of the freeze dried complex with 100 mg of corn starch, 120 mg of lactose, and 1 mg of light anhydrous silicic acid. An enteric capsules was prepared by applying an enteric coating of hydroxypropyl methyl cellulose phthalate on the capsules.

EXAMPLE 14

Production of tablets

The fibrinophilic urokinase complex obtained in Example 1 was freeze dried. Tablets were obtained by punching a mixture of 60,000 units of the freeze dried complex with 100 mg of lactose, 30 mg of corn starch, 80 mg of talc, and 2 mg of magnesium stearate. Enteric tables were produced by applying the same enteric coating as used in Example 14 on the tablets.

EXAMPLE 15

In vivo durability efficacy of fibrinophilic urokinase complex in beagles

A commercially available urokinase injections and the enteric capsulates of the fibrinophilic urokinase complex obtained in Example 14 were independently administered intraduodenally or intravenously for comparison of the durability of efficacy.

Samples of the commercially available urokinase injections and the enteric capsules of the fibrinophilic urokinase complex were independently administered in a dose of 60,000 units into the duodenal track of beagles weight about 10 kg each. Separately, samples of the commercially available urokinase agent were intravenously administered. After the administration, blood was collected from the vein of the forearm into a 3.8% citric acid (1/10 in volume) and centrifuged at 4° C. at 3,000 rpm for 10 minutes to obtain blood plasma. The blood plasma was tested for $\alpha_2$-PI content (amount of $\alpha_2$-plasmin inhibitor) by the use of a synthetic substrate S-2251.

Figure 4:
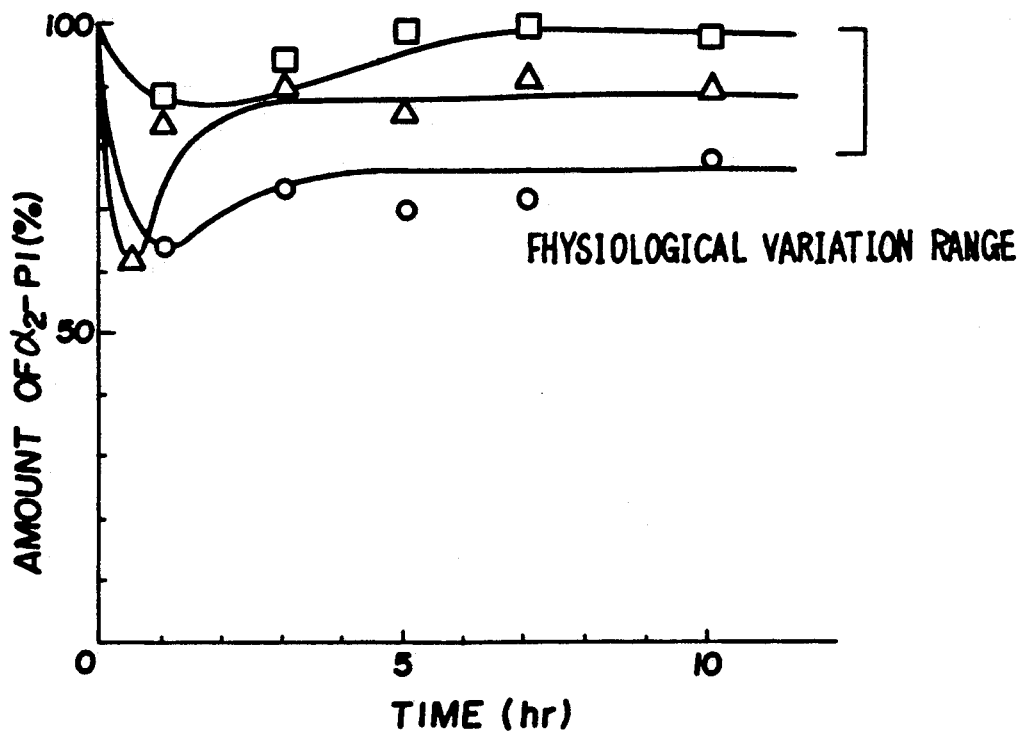
FIG. 4 is a graph showing durations of efficacy in beagles of a capsulated enteric preparation of the fibrinophilic urokinase complex and a commercially available urokinase preparation for injection. In the graph, the line connecting empty circles (o) represents the data obtained of the. capsulated enteric preparation of the fibrinophilic urokinase complex, the line connecting empty squares (□) the data of the commercially available urokinase preparation administered to the duodenal tube, and the line connecting empty triangles (Δ) the data of the commercially available urokinase injection preparation administered intravenously.

The results are shown in FIG. 4. When the commercially available urokinase injections was administered into the duodenal track, it was absorbed very little and brought about no decrease of the $\alpha_2$-PI content. When it was administered intravenously, the $\alpha_2$-PI content abruptly fell but quickly returned to the original level. This observation indicates that the agent was destitute of durability. When the enteric cupsules of the fibrinophilic urokinase complex was administered, the $\alpha_2$-PI content fell to the maximum of 60% in one hour and remained at that level for more than 8 hours.

EXAMPLE 16

Method for Production of fibrinophilic urokinase complex antiserum

The fibrinophilic urokinase complex obtained in Example 1 was intimately mixed equivoluminally with Freund's adjuvant and the mixture was injected in a dose of 1 to 2 ml into hares for immunization. After elapse of 4 weeks, the hares were given additional immunization by repeating the procedure. After elapse of two to three weeks, blood was collected from each hare to obtain antiserum against the fibrinophilic urokinase complex.

By the use of this rabbit antiserum, the antigen content of the fibrinophilic urokinase complex in the urine and the antigen content of the fibrinophilic urokinase complex in the blood can be measured by the Laurel method or the primary immune diffusion method.

INDUSTRIAL APPLICABILITY

The fibrinophilic urokinase complex of the present invention has high affinity for fibrin and enjoys satisfactory stability in the blood and, therefore, acts efficiently as an activator for plasminogen and manifest an outstanding ability to lysis fibrin. Thus, it provides an extremely high clinical effect. The fibrinophilic urokinase complex of this invention, therefore, can be advantageously used as a thrombolytic agent for the treatment of such thromboses as cerebral thrombosis, cardiac infarction, and pulmonary embolism.

Further, the method of this invention for the production of fibrinophilic urokinase complex permits the fibrinophilic urokinase complex to be produced with high purity and in high yields economically in large amounts and contributes greatly to the cure of thrombosis.

Since the antigen content of fibrinophilic urokinase complex in the urine can be determined by the use of an antiserum relative to the fibrinophilic urokinase complex, the determination will lend itself to the elucidation of the interrelation between various disease symptoms and disorders. The therapy with urokinase or with a tissue plasminogen activator can be carried out more effectively by monitoring the change of fibrinophilic urokinase complex in the blood.

It is claimed:

1. A purified urokinase complex substantially free of urine, said complex comprising urokinase and a urokinase inhibitor, said complex having a molecular weight of 97,500±3,000, and said complex having plasminogen activator activity and fibrin affinity.

2. A thrombolytic agent containing a purified urokinase complex substantially free of urine, said complex comprising urokinase and a urokinase inhibitor, said complex having a molecular weight of 97,500±3,000, and said complex having plasminogen activator activity and fibrin affinity.

3. A thrombolytic agent according to claim 2, said agent further comprising a suitable amount of a pharmaceutically acceptable vehicle.

4. A thrombolytic agent according to claim 2, said agent being provided in a form suitable for intravenous administration.

5. A thrombolytic agent according to claim 4, said administration comprising injection or drip infusion.

6. A thrombolytic agent according to claim 2, said agent being provided in a form suitable for oral administration.

7. A thrombolytic agent according to claim 6, said agent being provided in the form of capsules, tablets, pills, granules, subtilized granules, or powder.

8. A thrombolytic agent according to claim 6, said agent being provided in a form suitable for enteric delivery.

* * * * *